(12) United States Patent
Ueki

(10) Patent No.: US 8,702,595 B2
(45) Date of Patent: Apr. 22, 2014

(54) INSERTION INSTRUMENT ENDOSCOPE

(75) Inventor: Ryo Ueki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 426 days.

(21) Appl. No.: 13/084,661

(22) Filed: Apr. 12, 2011

(65) Prior Publication Data

US 2011/0282153 A1    Nov. 17, 2011

Related U.S. Application Data

(63) Continuation of application No. PCT/JP2010/071824, filed on Dec. 6, 2010.

(30) Foreign Application Priority Data

Jan. 29, 2010   (JP) .................................. 2010-019170

(51) Int. Cl.
*A61B 1/00*         (2006.01)

(52) U.S. Cl.
USPC ........... 600/149; 600/144; 600/146; 600/148; 600/150

(58) Field of Classification Search
USPC .................................. 600/144, 146, 148–150
See application file for complete search history.

(56) References Cited

U.S. PATENT DOCUMENTS

| | | | | |
|---|---|---|---|---|
| 3,610,231 A | * | 10/1971 | Takahashi et al. | 600/139 |
| 3,799,151 A | * | 3/1974 | Fukaumi et al. | 600/142 |
| 4,203,430 A | * | 5/1980 | Takahashi | 600/149 |
| 4,351,323 A | * | 9/1982 | Ouchi et al. | 600/142 |
| 4,748,969 A | * | 6/1988 | Wardle | 600/150 |
| 4,841,950 A | | 6/1989 | Fukuda | |
| 5,167,221 A | * | 12/1992 | Chikama | 600/149 |
| 5,179,935 A | * | 1/1993 | Miyagi | 600/142 |
| 6,811,532 B2 | * | 11/2004 | Ogura et al. | 600/146 |
| 8,133,171 B2 | * | 3/2012 | Barry et al. | 600/151 |
| 8,366,606 B2 | * | 2/2013 | Watanabe et al. | 600/144 |
| 2002/0017515 A1 | * | 2/2002 | Obata et al. | 219/137 R |
| 2004/0242966 A1 | * | 12/2004 | Barry et al. | 600/146 |

(Continued)

FOREIGN PATENT DOCUMENTS

| | | |
|---|---|---|
| EP | 2 067 433 A1 | 6/2009 |
| EP | 2 116 170 A1 | 11/2009 |

(Continued)

OTHER PUBLICATIONS

European Search Report dated Mar. 21, 2012 from corresponding European Patent Application No. EP 10 84 4691.5.

*Primary Examiner* — Matthew J Kasztejna
(74) *Attorney, Agent, or Firm* — Scully, Scott, Murphy & Presser, P.C.

(57) ABSTRACT

An insertion instrument and an endoscope are provided that include: a bending portion provided in an insertion portion; a flexible tube portion connected in series to a proximal end side of the bending portion; an inside guide pipe provided inside the insertion portion, and inside which a wire is inserted to freely advance and retract; and an outside guide pipe provided inside the insertion portion, and inside which the inside guide pipe is inserted to freely advance and retract. Inside the insertion portion, a distal end of the inside guide pipe is fixed to a midway position of the bending portion, and a proximal end of the inside guide pipe is configured to be switchable between a fixed state and a non-fixed state. Further, inside the insertion portion, a distal end of the outside guide pipe is fixed to a distal end of a flexible tube portion, and a proximal end thereof is fixed at a more rearward position than the flexible tube portion.

10 Claims, 11 Drawing Sheets

(56) References Cited

U.S. PATENT DOCUMENTS

| | | |
|---|---|---|
| 2006/0200000 A1* | 9/2006 | Sato et al. .................. 600/146 |
| 2009/0143647 A1 | 6/2009 | Banju |
| 2010/0004508 A1 | 1/2010 | Naito et al. |

FOREIGN PATENT DOCUMENTS

| | | |
|---|---|---|
| JP | 63-154151 | 6/1988 |
| JP | 01-104237 | 4/1989 |
| JP | 04-051929 | 2/1992 |
| JP | 08-171058 | 7/1996 |
| JP | 10-248794 | 9/1998 |
| JP | 11-262470 | 9/1999 |
| JP | 11-267092 | 10/1999 |
| JP | 2005-185526 | 7/2005 |
| JP | 2005-279124 | 10/2005 |
| JP | 2008-253774 | 10/2008 |
| JP | 2009-153959 | 7/2009 |

* cited by examiner

40(40m)  50(50m)

40m
40
50
50m

INSERTION INSTRUMENT ENDOSCOPE

CROSS REFERENCE TO RELATED APPLICATION

This application is a continuation application of PCT/JP2010/071824 filed on Dec. 6, 2010 and claims benefit of Japanese Application No. 2010-019170 filed in Japan on Jan. 29, 2010, the entire contents of which are incorporated herein by this reference.

BACKGROUND OF THE INVENTION

1. Field of the Invention

The present invention relates to an insertion instrument and an endoscope that has an elongated insertion portion that is inserted into a subject, and a bendable bending portion that is provided in the insertion portion and that bends accompanying pulling/relaxing of a wire that is passed through the insertion portion.

2. Description of the Related Art

In recent years, an insertion instrument, for example, an endoscope, that is inserted inside a subject or an object is being widely used in a medical field and an industrial field. An endoscope used in the medical field observes an organ inside a body cavity of a subject by inserting an elongated insertion portion into the body cavity. As necessary, the endoscope can perform various kinds of treatment using a treatment instrument that is inserted inside a treatment instrument insertion channel provided in the endoscope.

Further, with an endoscope used in the industrial field, by inserting an elongated insertion portion of the endoscope inside an object such as a jet engine or pipes of a factory, it is possible to conduct an observation to check for the presence of flaws or corrosion or the like at a site to be examined inside the object and to perform various kind of repairs.

A configuration is known in which a bending portion that is bendable in a plurality of directions is provided in an insertion portion of an endoscope. The bending portion improves the advancing ability of the insertion portion at a curved section inside a duct, and also varies an observation direction of an observation optical system provided in a distal end portion that is positioned further on a distal end side in the insertion direction (hereunder, referred to simply as "distal end side") than the bending portion in the insertion portion.

Normally, a bending portion provided in an insertion portion of an endoscope is configured to be bendable in, for example, four directions, namely, upward, downward, left, and right, by connecting a plurality of bending pieces along the insertion direction of the insertion portion.

Further, the bending portion is configured to be bendable in any of the upward, downward, left, and right directions by performing a pulling operation from an operation portion with respect to any of four wires that are passed through the inside of the insertion portion and whose distal ends are fixed to a bending piece that is positioned furthest on the distal end side among the bending pieces.

In this connection, the reason that only the bending portion bends accompanying an operation to pull a wire is that, in the insertion portion, an outer circumference of the wire that is inside a flexible tube portion which exhibits flexibility that is positioned further on a proximal end side in the insertion direction (hereunder, referred to simply as "proximal end side") than the bending portion is covered by a coil pipe or the like in a state in which a distal end and a proximal end thereof in the insertion direction are fixed inside the flexible tube portion. Another reason is that, even if a wire is pulled, the coil pipe resists a compressive force that is applied to the coil pipe along an extending direction of the coil pipe.

In this connection, a bending portion that has a short length in the insertion direction, that is, a bending portion with a small bending radius, is capable of small adjustments. Hence, such a bending portion is advantageous because the ability of the distal end portion of the insertion portion to pass through a curved section inside a duct is enhanced thereby, and an observation optical system provided in the distal end portion can be easily brought close to a site to be examined.

This is because, when a bending portion has a long length, for example, if the endoscope in question is a medical endoscope, when the endoscope is inserted into the colon, at a curved section of the colon the distal end portion is liable to contact the curved section and the field of view will be lost. More specifically, when a short bending portion is used, the distal end portion is not liable to contact against an intestinal wall at a curved section. Note that the number of connected bending pieces may be decreased to shorten the length of the bending portion.

Further, with a medical endoscope, a technique is commonly used in which, after the distal end portion passes through a curved section, the curved section is straightened by drawing in the proximal end side of the insertion portion in a state in which the distal end portion and the bending portion are hooked to tissue inside the body cavity, and thereafter the bending portion is caused to pass through the curved section by pushing in the insertion portion from the proximal end side.

Japanese Patent Application Laid-Open Publication No. 10-248794 discloses a configuration and technique that enhance the insertability of an insertion portion into the colon by first inserting a known overtube into a body cavity, and thereafter inserting the insertion portion into the overtube.

In addition, Japanese Patent Application Laid-Open Publication No. 2008-253774 discloses a configuration in which a first bending portion and a second bending portion are provided as two bending portions on a distal end side of an insertion portion. More specifically, the second bending portion is formed with a more rigid configuration than the first bending portion at a position that is further on the proximal end side than the first bending portion.

Furthermore, Japanese Patent Application Laid-Open Publication No. 2005-185526 discloses a configuration in which two shape memory alloys whose rigidity increases accompanying the supply of a current thereto are provided along the insertion direction inside a bending portion that is positioned on a distal end side of an insertion portion.

Japanese Patent Application Laid-Open Publication No. 10-248794 also discloses a configuration that avoids the occurrence of a sticking phenomenon by decreasing friction with the colon by causing an insertion portion to vibrate using a vibration unit.

SUMMARY OF THE INVENTION

An insertion instrument according to one aspect of the present invention includes: an elongated insertion portion that is inserted inside a subject; a bending portion that is provided in the insertion portion and that is capable of bending accompanying pulling/relaxing of a wire that is inserted through the inside of the insertion portion; a flexible tube portion that is connected in series to a proximal end side of the bending portion in the insertion portion in an insertion direction of the insertion portion; an inside guide pipe that is flexible and that is provided inside the insertion portion, and through the inside of which the wire is inserted to freely advance and retract in the insertion direction; and an outside guide pipe that is flexible and that is provided inside the insertion portion, and through the inside of which the inside guide pipe is inserted to freely advance and retract in the insertion direction; wherein: inside the insertion portion, a distal end in the insertion direction of the inside guide pipe is fixed to a midway position in the insertion direction of the bending portion, and a proximal end in the insertion direction of the inside guide pipe is configured to be switchable between a fixed state and a non-fixed state; and inside the insertion portion, a distal end in the insertion direction of the outside guide pipe is fixed to a distal end of the flexible tube portion, and a proximal end in the insertion direction is fixed at a more rearward position in the insertion direction than the flexible tube portion.

An endoscope according to another aspect of the present invention has the configuration of the insertion instrument according to the above described first aspect.

DETAILED DESCRIPTION OF THE PREFERRED EMBODIMENT

An embodiment of the present invention is described hereunder with reference to the drawings. It should be noted that the drawings are schematic ones in which the relationship between the thickness and width of each member, the thickness ratios of the members, and the like are different from those of actual members. Naturally, the drawings include portions in which the dimensional relationships and ratios are different from one another.

Figure 1:
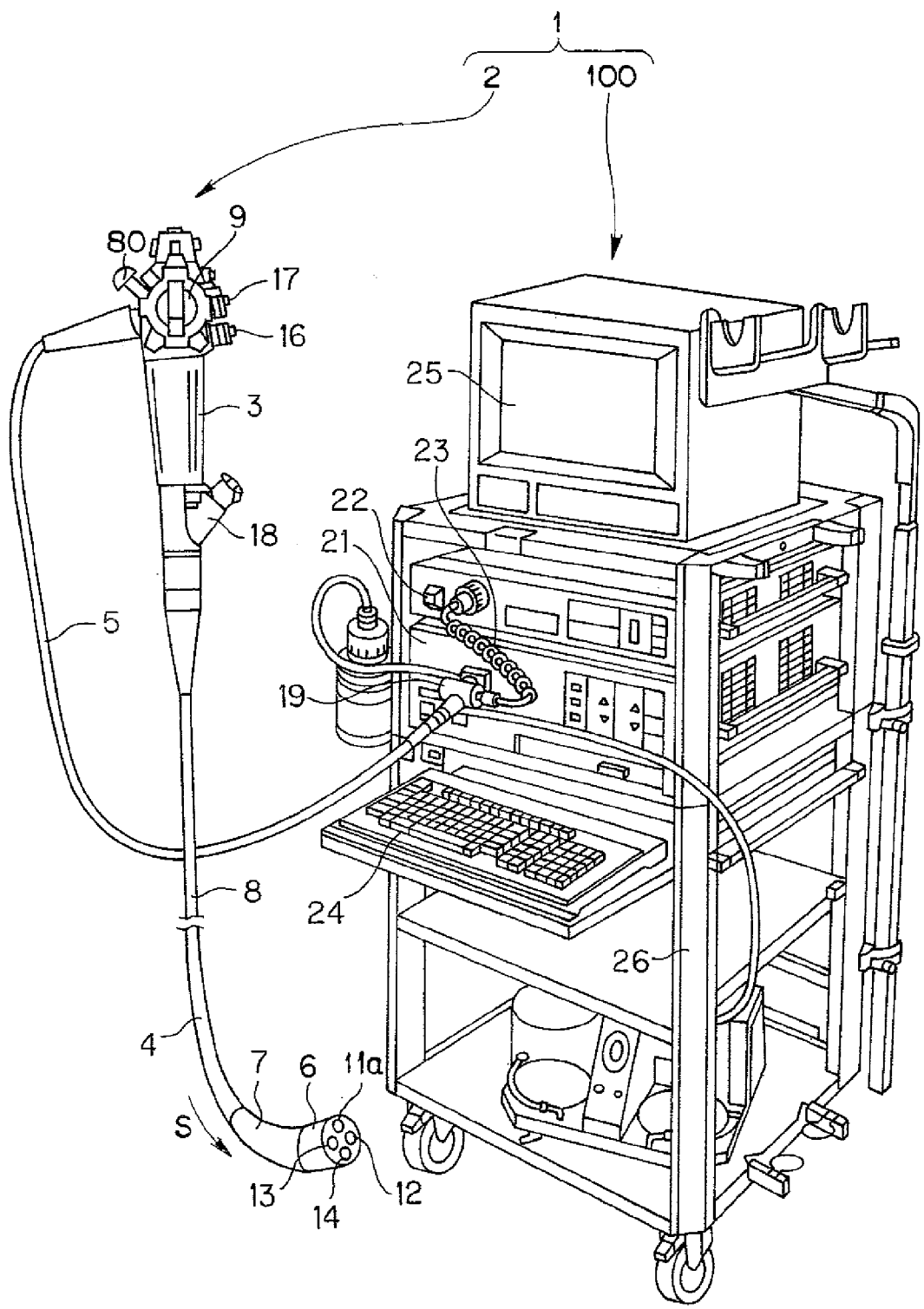
FIG. 1 is a perspective view that illustrates the external appearance of an endoscope apparatus including an endoscope that shows the present embodiment.

FIG. 1 is a perspective view that illustrates the external appearance of an endoscope apparatus including an endoscope that shows the present embodiment.

As shown in FIG. 1, an endoscope apparatus 1 includes an endoscope 2 and a peripheral apparatus 100 as principal components. The endoscope 2 includes an operation portion 3, an insertion portion 4 that is inserted into a subject, a universal cord 5, and a connector 19 as principal components.

The peripheral apparatus 100 includes, as principal components, a light source apparatus 21, a video processor 22, a connection cable 23, a keyboard 24, and a monitor 25, all of which are placed on a stand 26. The endoscope 2 and the peripheral apparatus 100 configured as described above are connected to each other through the connector 19.

The operation portion 3 of the endoscope 2 is provided with a bending operation knob 9, an air supply/water supply operation button 16, a suction operation button 17, a treatment instrument insertion port 18, and a fixing lever 80 that is described later.

The insertion portion 4 of the endoscope 2 includes a distal end portion 6, a bending portion 7, and a flexible tube portion 8, and is formed in an elongated shape along an insertion direction S.

The bending portion 7 is caused to bend by a bending operation by the bending operation knob 9 provided at the operation portion 3, and is provided between the distal end portion 6 and the flexible tube portion 8 on the distal end side in the insertion direction S (hereunder, referred to simply as "distal end side") of the insertion portion 4 so as to be bendable in, for example, four directions, namely, upward, downward, left and right, accompanying pulling/relaxing of wires 30 (see FIG. 2), described below, that are inserted through the insertion portion 4, in accordance with a bending operation of the bending operation knob 9.

An objective lens 11a of an unshown image pickup unit that is provided inside the distal end portion 6 is provided at a distal end face on the distal end side of the distal end portion 6. A distal end opening 12 of an unshown channel that supplies a fluid towards a site to be examined inside the subject, an illuminating window 13 for illuminating the inside of the subject, and a distal end opening 14 of an unshown treatment instrument insertion channel are also provided in the distal end face on the distal end side of the distal end portion 6.

The distal end opening 12 is used to selectively eject air and liquid in accordance with an operation of the air supply/water supply operation button 16 of the operation portion 3. The distal end opening 14 is used to selectively recover mucus and the like in a body cavity via the treatment instrument insertion channel in accordance with an operation of the suction operation button 17 of the operation portion 3. Further, various kinds of treatment instruments that are inserted from the treatment instrument insertion port 18 are projected out from the distal end opening 14 towards a site to be examined.

The connector 19 is provided at the distal end of the universal cord 5 of the endoscope 2. The connector 19 is connected to the light source apparatus 21 of the peripheral apparatus 100. Various kinds of pipe sleeves and various kinds of electric contact points which are not shown in the drawings are provided in the connector 19. The video processor 22 is also connected to the connector 19 via the connection cable 23.

Figure 2:
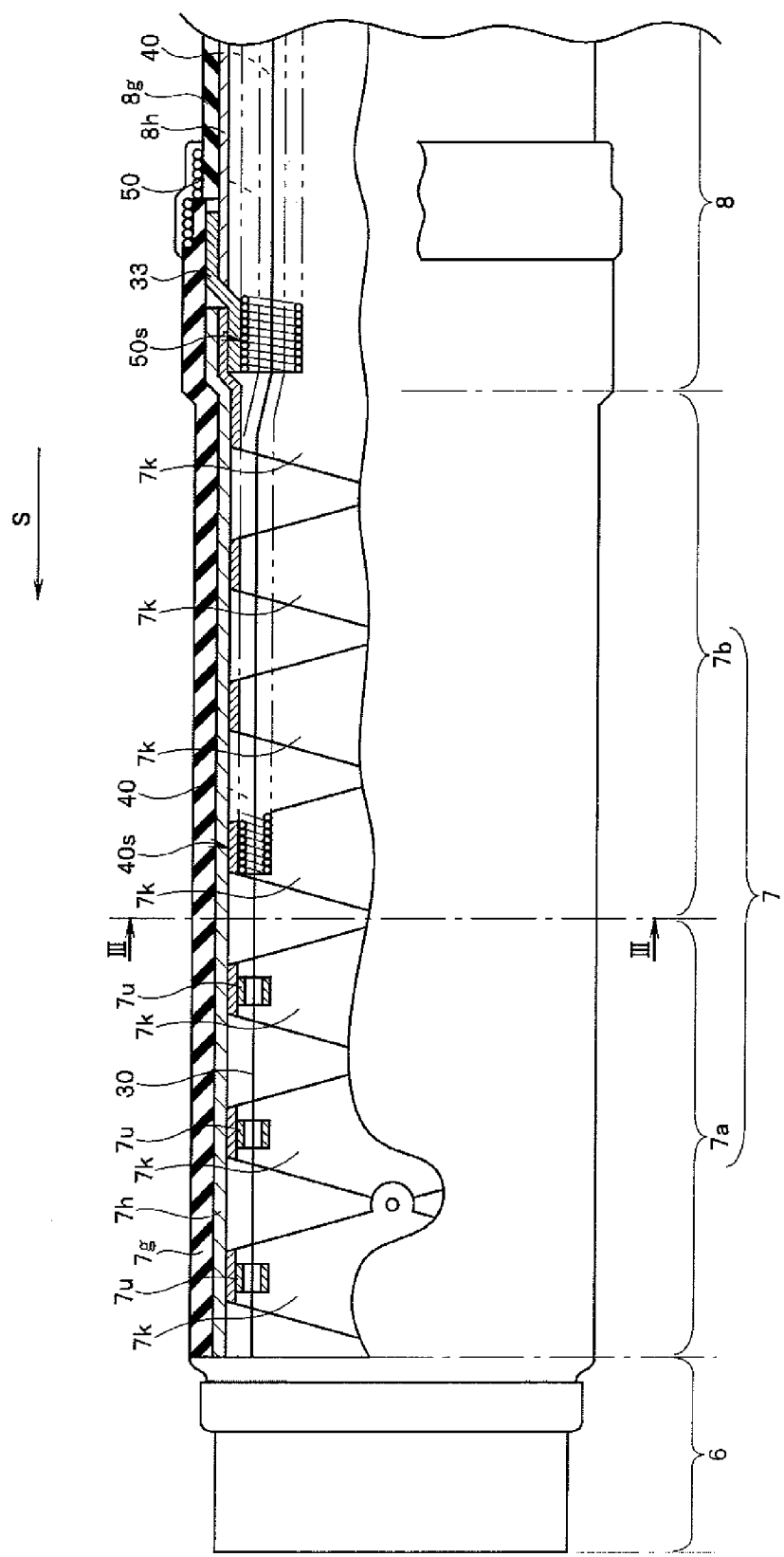
FIG. 2 is a partial cross-sectional view that schematically shows an internal configuration of a distal end side of an insertion portion shown in FIG. 1.
Figure 3:
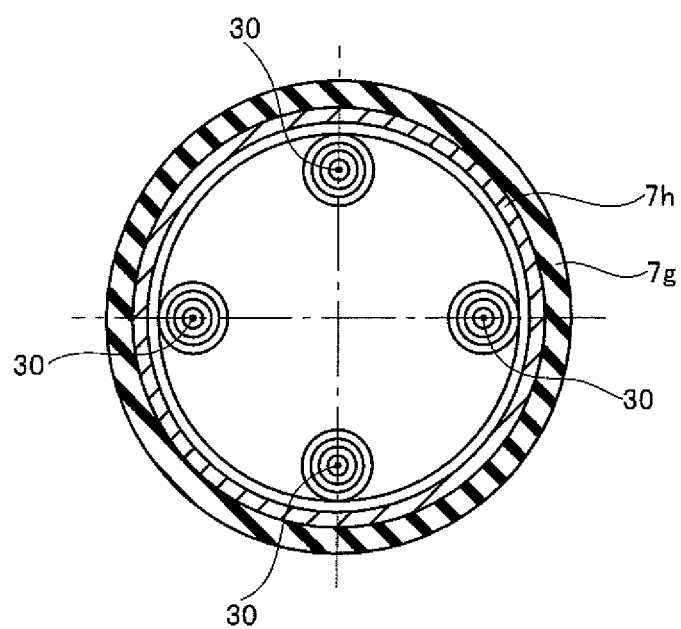
FIG. 3 is a cross-sectional view of a bending portion along a line III-III in FIG. 2.

Next, the configurations inside the operation portion 3 and the insertion portion 4 are described using FIG. 2 to FIG. 6. FIG. 2 is a partial cross-sectional view that schematically shows the internal configuration of the distal end side of the insertion portion shown in FIG. 1. FIG. 3 is a cross-sectional view of a bending portion along a line III-III in FIG. 2.

Figure 4:
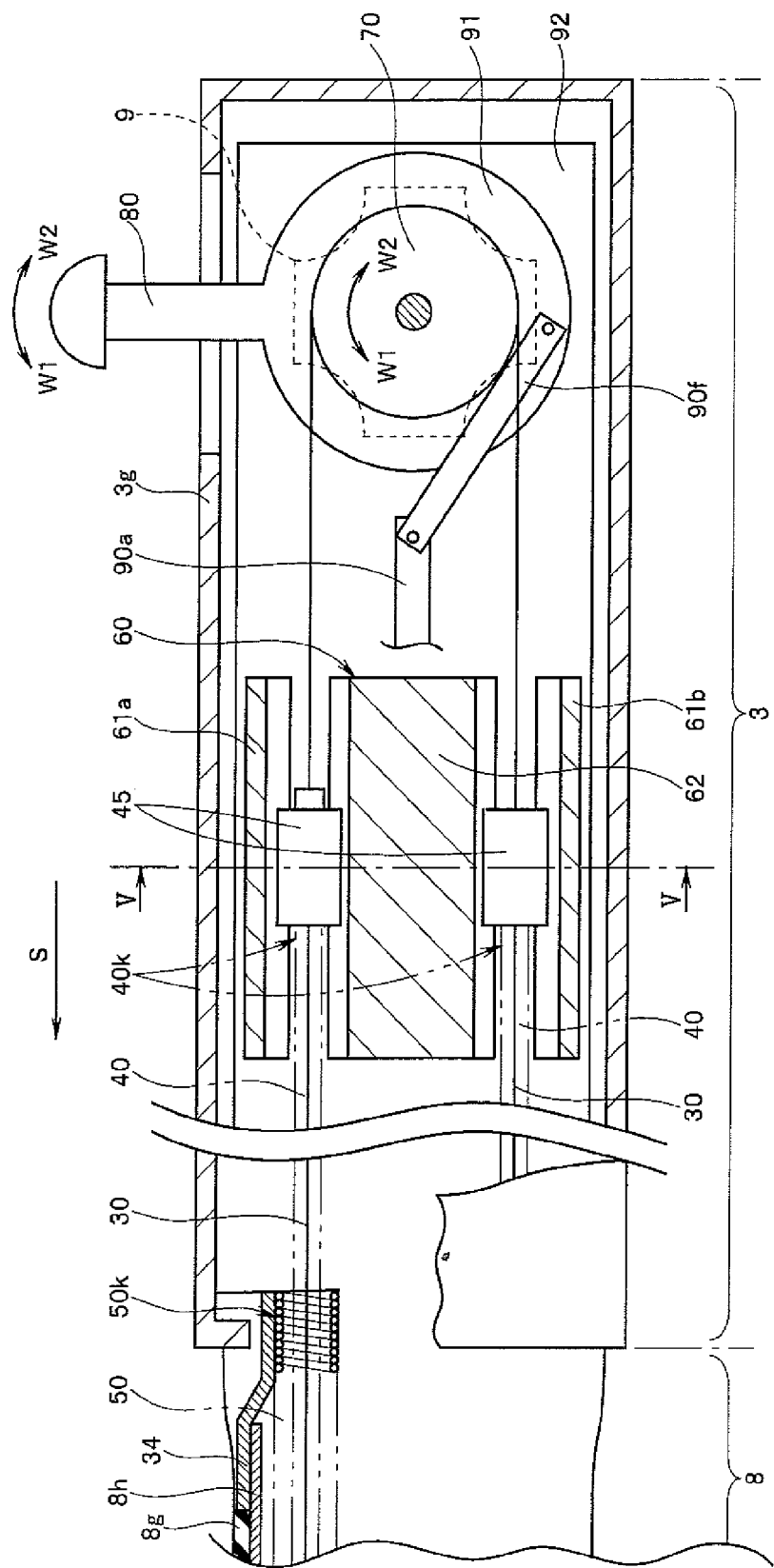
FIG. 4 is a partial cross-sectional view that schematically shows an internal configuration of a proximal end side of the insertion portion and an operation portion that are shown in FIG. 1.
Figure 5:
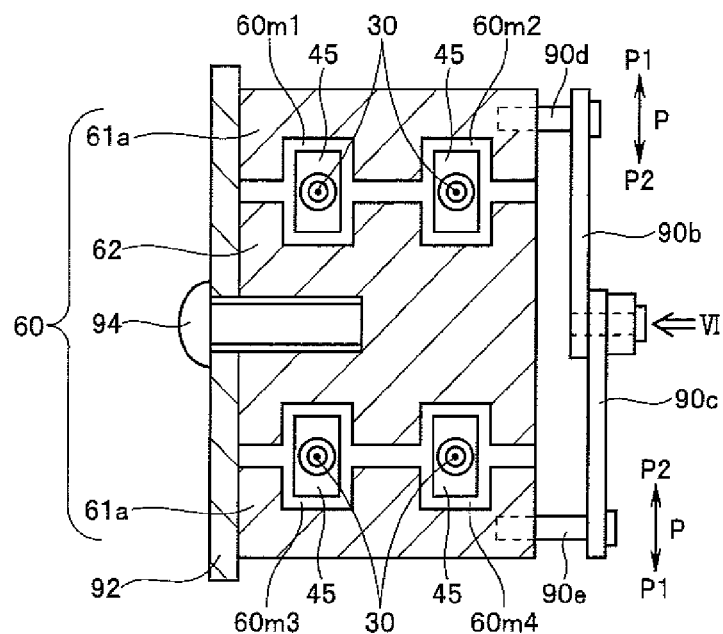
FIG. 5 is a cross-sectional view of the operation portion along a line V-V in FIG. 4.
Figure 6:
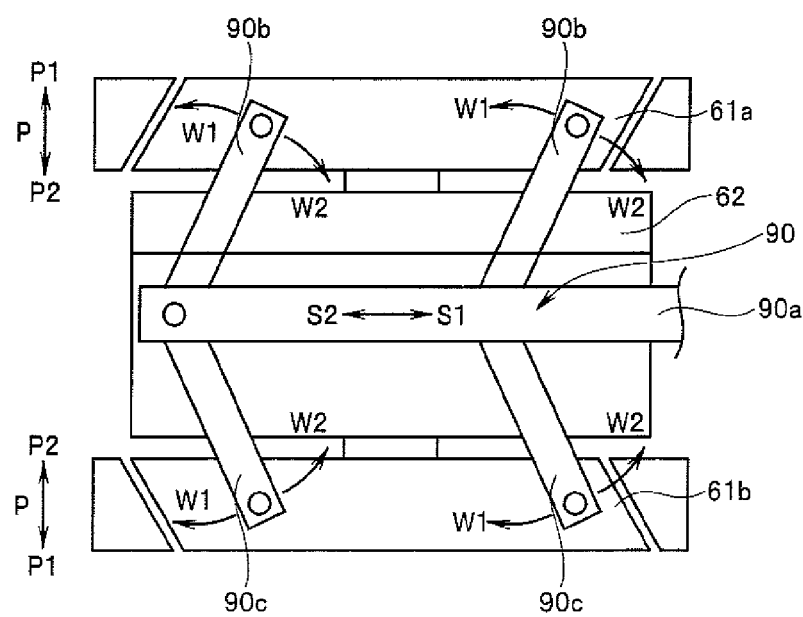
FIG. 6 is a side view that shows the operation portion illustrated in FIG. 5 as viewed from a direction VI in FIG. 5.

FIG. 4 is a partial cross-sectional view that schematically shows the internal configuration of the proximal end side of the insertion portion and the operation portion that are shown in FIG. 1. FIG. 5 is a cross-sectional view of the operation portion along a line V-V in FIG. 4. FIG. 6 is a side view that shows the operation portion of FIG. 5 as viewed from a direction VI in FIG. 5.

As shown in FIG. 2, a plurality of bending pieces 7k are provided in a linked manner along the insertion direction S inside the bending portion 7. The outer circumferences of the plurality of bending pieces 7k are covered with a braid 7h, and the outer circumference of the braid 7h is covered with a bending rubber 7g. Hereunder, a region located in a front half part in the insertion direction S in the bending portion 7 is referred to as a first region 7a, and a region located in a rear half part in the insertion direction S in the bending portion 7 is referred to as a second region 7b.

As shown in FIG. 3, wire guides 7u that hold, for example, four wires 30 that are inserted through the inside of the operation portion 3 and the insertion portion 4 are respectively provided in the plurality of bending pieces 7k located in the first region 7a. Four of the wire guides 7u are provided in each bending piece 7k at staggered positions in the circumferential direction of the bending portion 7.

The distal ends of the respective wires 30 are fixed at staggered positions in the circumferential direction of the bending portion 7 to the bending piece 7k located at the farthest position on the distal end side in the insertion direction S among the plurality of bending pieces 7k.

As shown in FIG. 4, the respective proximal ends of two of the wires 30 for upward and downward bending are wound around a sprocket 70 that is connected to the bending operation knob 9. Further, the respective proximal ends of two of the wires 30 for left and right bending are wound around an unshown sprocket that is different from the sprocket 70 which is connected to the bending operation knob 9.

In the second region 7b, a distal end side of a connecting member 33 is fixed to the bending piece 7k located at the farthest position on the proximal end side among the plurality of bending pieces 7k. A distal end side of a braid 8h that is included in the flexible tube portion 8 is fixed to the outer circumference of the proximal end side of the connecting member 33. The outer circumference of the braid 8h is covered by a covering tube 8g.

Further, as shown in FIG. 4, the distal end side of a connecting member 34 is fixed to the outer circumference of the proximal end side of the braid 8h, and a sheath member 3g of the operation portion 3 is fixed to the outer circumference of the proximal end side of the connecting member 34.

As shown in FIG. 2 and FIG. 4, the outer circumferences of the four wires 30 that are inserted through the inside of the operation portion 3 and the insertion portion 4 are respectively covered by an inside guide pipe 40 that is constituted by, for example, a flexible coil pipe.

More specifically, four of the inside guide pipes 40 are inserted through the inside of the operation portion 3 and the insertion portion 4 at staggered positions in the circumferential direction of the insertion portion 4. In this connection, the respective wires 30 that are inserted through the respective inside guide pipes 40 are arranged to freely advance and retract in the insertion direction S.

The reason the inside guide pipes 40 are constituted by a flexible coil pipe is that if the outer circumference of each wire 30 is covered by an ordinary hard pipe made of metal, not only will the bending portion 7 no longer bend, but the flexibility of the flexible tube portion 8 will decrease.

Hence, a member constituting the inside guide pipe 40 is not limited to a coil pipe as long as the member does not reduce the bendability of the bending portion 7 and the flexibility of the flexible tube portion 8 and can resist a compressive force that acts along an extension direction of the inside guide pipe 40 that is parallel to the insertion direction S as described later when the bending portion 7 bends.

Further, as shown in FIG. 2, a distal end 40s of the inside guide pipe 40 is fixed by, for example, brazing to the braid 7h at a midway position, for example, a distal end position of the second region 7b, in the insertion direction S of the bending portion 7.

In this connection, a proximal end 40k of the inside guide pipe 40 is configured to be switchable between a fixed state and a non-fixed state by a fixing switching member 60 provided inside the operation portion 3. The fixing switching member 60 is described later.

Furthermore, as shown in FIG. 2 and FIG. 4, the outer circumferences of the four inside guide pipes 40 positioned inside the flexible tube portion 8 are respectively covered by outside guide pipes 50 constituted by, for example, a flexible coil pipe. Each of the inside guide pipes 40 that are inserted through the inside of the respective outside guide pipes 50 are configured to freely advance and retract in the insertion direction S.

Note that the outside guide pipes 50 need not cover the outer circumferences of all four of the inside guide pipes 40. For example, a configuration may be adopted in which the outside guide pipe 50 covers only the outer circumference of the inside guide pipe 40 that covers the outer circumference of the wire 30 that causes the bending portion 7 to bend in the upward direction. In such a case, it is sufficient that the distal end 40s and proximal end 40k of each of the three inside guide pipes 40 that are not covered by an outside guide pipe 50 are fixed.

The reason the outside guide pipe 50 is constituted by a flexible coil pipe is that if the outer circumference of the inside guide pipe 40 is covered by an ordinary hard pipe made of metal, the flexibility of the flexible tube portion 8 will decrease.

Hence, a member constituting the outside guide pipe 50 is not limited to a coil pipe as long as the member does not reduce the flexibility of the flexible tube portion 8 and can resist a compressive force that acts along an extension direction of the outside guide pipe 50, that is described later, when the bending portion 7 bends.

A distal end 50s of the outside guide pipe 50 is fixed by, for example, brazing to the distal end of the flexible tube portion 8, more specifically, to the proximal end side of the connecting member 33. Further, a proximal end 50k of the outside guide pipe 50 is fixed by, for example, brazing at a position that is further to the rear in the insertion direction S than the flexible tube portion 8, more specifically, to the proximal end side of the connecting member 34.

Thus, because the outside guide pipes 50 are inserted through the flexible tube portion 8 in a state in which the distal end 50s and the proximal end 50k of each outside guide pipe 50 are fixed, when any one of the wires 30 is pulled to bend the bending portion 7, the relevant outside guide pipe 50 resists a compressive force that acts on the flexible tube portion 8 along an extension direction of the relevant outside guide pipe 50. It is thus possible to prevent the flexible tube portion 8 that exhibits flexibility from bending together with the bending portion 7.

Note that, the inside guide pipes 40 are formed to a length along the insertion direction S such that, in a state in which the distal ends 40s of the inside guide pipes 40 are fixed at the distal end of the second region 7b, and the distal ends 50s and the proximal ends 50k of the outside guide pipes are fixed, the proximal ends 40k of the inside guide pipes 40 are not drawn further to the distal end side than the proximal ends 50k of the outside guide pipes 50.

Next, an example of the fixing switching member 60 at the proximal ends 40k of the inside guide pipes 40 is described using FIG. 4 to FIG. 6.

As shown in FIG. 4 and FIG. 5, inside the operation portion 3, the fixing switching member 60 is provided by being fixed by, for example, a screw 94 to a bottom plate 92 that is fixed to the sheath member 3g.

As shown in FIG. 5, principal components of the fixing switching member 60 include a substrate 62 to which the screw 94 is fixed, and two moving members 61a and 61b that are movable in a P1 direction or a P2 direction with respect to a top surface and a bottom surface of the substrate 62 in a P direction that is perpendicular to the insertion direction S.

Further, two grooves 60m1 and 60m2 along the insertion direction S through which two wires 30, inside guide pipes 40 that respectively cover the outer circumferences of the two wires 30, and pipe stoppers 45 that are fixed to the respective proximal ends 40k of the inside guide pipes 40 can be freely inserted, respectively, are formed between the top surface of the substrate 62 and the moving member 61a that faces the top surface. In this connection, each of the wires 30 is movable in the insertion direction S inside the relevant pipe stopper 45.

Further, two grooves 60m3 and 60m4 along the insertion direction S through which two wires 30, inside guide pipes 40 that respectively cover the outer circumferences of the two wires 30, and pipe stoppers 45 that are fixed to the respective proximal ends 40k of the inside guide pipes 40 can be freely inserted, respectively, are formed between the bottom surface of the substrate 62 and the moving member 61b that faces the bottom surface.

The reason four grooves are provided along the insertion direction S in the fixing switching member 60 is to prevent the positions of the four wires 30 from being disarranged due to the four wires 30 touching each other inside the operation portion 3. More specifically, the four grooves are provided along the insertion direction S to regulate the positions of the four wires 30 inside the operation portion 3.

The fixing switching member 60 is formed along the insertion direction S to a length such that the pipe stoppers 45 do not protrude from the distal ends and proximal ends of the grooves 60m1 to 60m4 when the respective pipe stoppers 45 perform an advancing and retracting movement together with the proximal end 40k of the relevant inside guide pipe 40 in the insertion direction S inside the four grooves 60m1 to 60m4. In this connection, each of the wires 30 is movable in the insertion direction S inside the relevant pipe stopper 45.

As shown in FIG. 5, a link mechanism 90 is provided on a face on a side that does not contact against the bottom plate 92 of the moving members 61a and 61b.

More specifically, the link mechanism 90 includes a joint 90a that is positioned along the insertion direction S, arm portions 90b that are rotatably connected to a distal end side of the joint 90a and which protrude at a predetermined angle in the P1 direction from the distal end side, and a joint 90d having one end rotatably connected to a protruding end of the respective arm portions 90b and another end rotatably connected to the moving member 61a.

The link mechanism 90 also includes arm portions 90c that are rotatably connected to the distal end side of the joint 90a so as to be on the same axis as the arm portions 90b, and that protrude at a predetermined angle in the P2 direction from the distal end side of the joint 90a, a joint 90e having one end rotatably connected to a protruding end of the respective arm portions 90c and another end rotatably connected to the moving member 61b, and a joint 90f having a distal end rotatably connected to a proximal end of the joint 90a and another end rotatably connected to a sprocket 91 that is connected to the fixing lever 80. In this connection, although the sprocket 91 is fixed on the same axis as the sprocket 70, the sprocket 91 may rotate independently from the sprocket 70.

Hence, first, when fixing the proximal ends 40k, that is, the pipe stoppers 45, of the inside guide pipes 40, the operator rotates the fixing lever 80 in a W2 direction. Thereafter, the sprocket 91 rotates in the W2 direction and, through the joint 90f, the joint 90a moves in an S2 direction and the arm portions 90b and 90c rotate in the W2 direction.

As a result, by the moving members 61a and 61b moving in the P2 direction, the four pipe stoppers 45 are respectively fixed between the top surface of the substrate 62 and the moving member 61a and between the bottom surface of the substrate 62 and the moving member 61b inside the respective grooves 60m1 to 60m4. More specifically, the proximal end 40k of each inside guide pipe 40 is fixed.

Subsequently, when releasing the fixed state of the proximal ends 40k, that is, the pipe stoppers 45, of the inside guide pipes 40, the operator rotates the fixing lever 80 in the W1 direction. Thereafter, the sprocket 91 rotates in a W1 direction and, through the joint 90f, the joint 90a moves in the S1 direction and the arm portions 90b and 90c rotate in the W1 direction.

As a result, by movement of the moving members 61a and 61b in the P1 direction, the fixed states of the four pipe stoppers 45 that are fixed between the top surface of the substrate 62 and the moving member 61a and between the bottom surface of the substrate 62 and the moving member 61b inside the respective grooves 60m1 to 60m4 are released. More specifically, the fixed state of the proximal end 40k of each inside guide pipe 40 is released.

Note that the above described configuration of the fixing switching member 60 at the proximal ends 40k of the inside guide pipes 40 that is illustrated in FIG. 4 to FIG. 6 is merely one example, and naturally a configuration may be adopted that has a different fixing mechanism.

Figure 7:
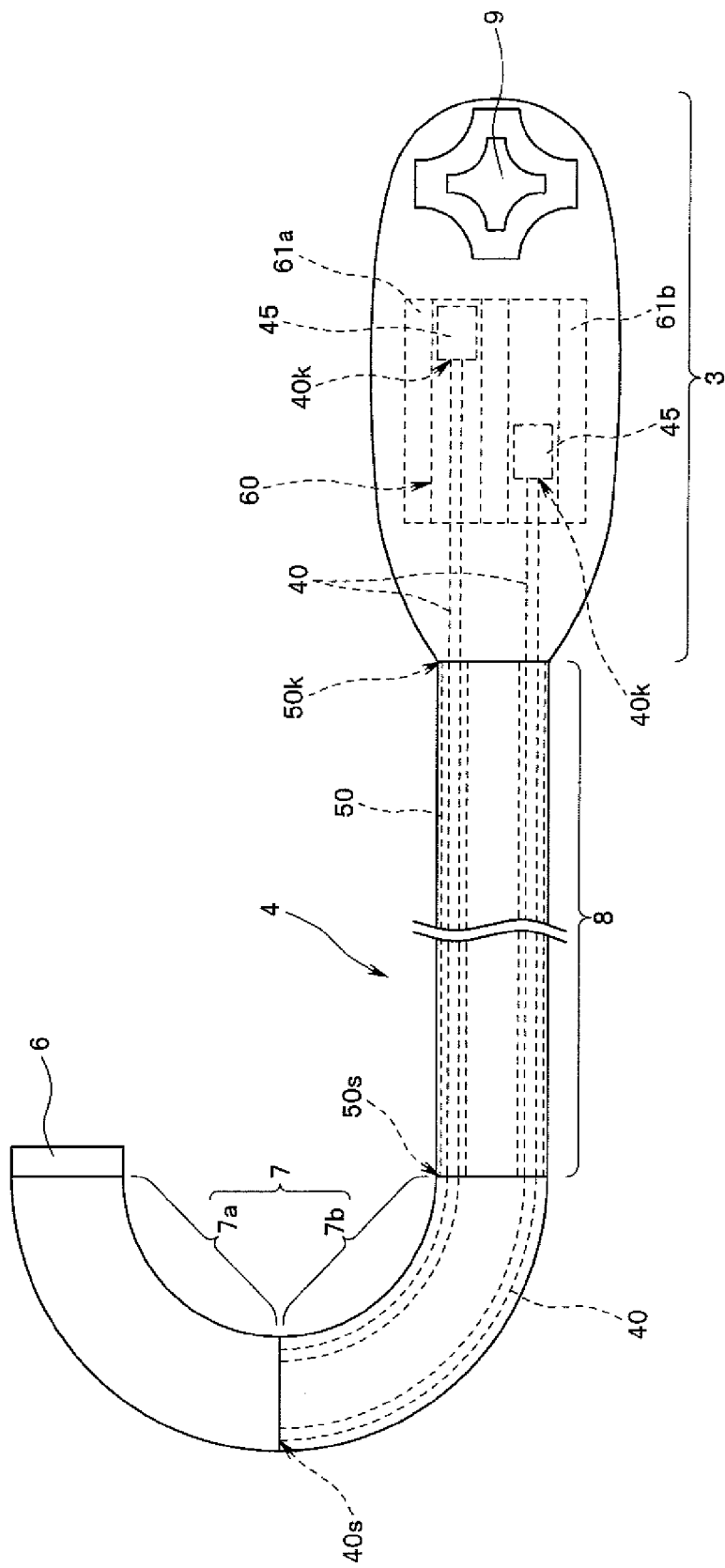
FIG. 7 is a view that schematically shows a state in which, with respect to the bending portion shown in FIG. 2, the bending portion is bent from a proximal end side of a second region.
Figure 8:
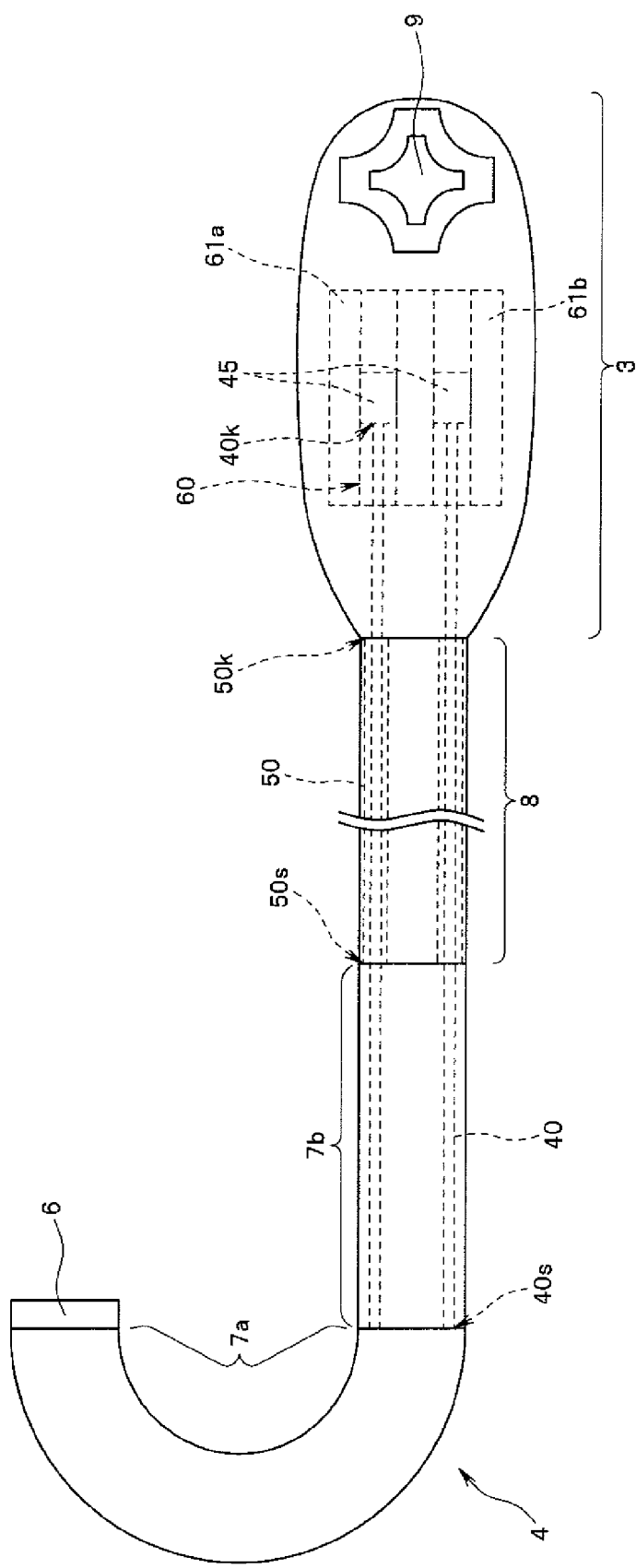
FIG. 8 is a view that schematically shows a state in which, with respect to the bending portion shown in FIG. 2, the bending portion is bent from a proximal end side of a first region.

Next, the operation of the present embodiment is described using FIG. 7 and FIG. 8. FIG. 7 is a view that schematically shows a state in which, with respect to the bending portion shown in FIG. 2, the bending portion is bent from the proximal end side of the second region. FIG. 8 is a view that schematically shows a state in which, with respect to the bending portion shown in FIG. 2, the bending portion is bent from the proximal end side of the first region.

First, if the operator wishes to bend the bending portion 7 from the proximal end side of the second region 7b, that is, if the operator wishes to bend the entire bending portion 7, as shown in FIG. 7, without operating the fixing lever 80, the operator releases the fixed state of the proximal ends 40k of the inside guide pipes 40 that are fixed using the fixing switching member 60.

In this state, when the operator operates the bending operation knob 9 to pull any one wire among the four wires, because the proximal ends 40k are not fixed, the inside guide pipes 40 can not resist a compressive force that acts along an extension direction of the inside guide pipes 40 in the second region 7b of the bending portion 7, and the proximal end 40k moves rearward in the insertion direction S in any one of the grooves 60m1 to 60m4 of the fixing switching member 60.

Further, because the distal ends 50s and proximal ends 50k of the outside guide pipes 50 are fixed inside the flexible tube portion 8, the outside guide pipes 50 resist a compressive force that acts along an extension direction of the outside guide pipes 50.

As a result, taking the distal ends of the outside guide pipes 50 as a starting point, the first region 7a and second region 7b of the bending portion 7 bend from the proximal end side of the second region 7b. More specifically, the entire bending portion 7 bends.

Next, if the operator wishes to bend only the first region 7a of the bending portion 7, as shown in FIG. 8, the operator operates the fixing lever 80 to fix the proximal ends 40k of the inside guide pipes 40 using the fixing switching member 60 as shown in FIG. 4 to FIG. 6.

In this state, when the operator operates the bending operation knob 9 to pull any one wire among the four wires, because the proximal ends 40k are fixed, the inside guide pipes 40 resist a compressive force that acts along the extension direction of the inside guide pipes 40 in the second region 7b of the bending portion 7.

As a result, taking the distal ends of the inside guide pipes 40 as a starting point, only the first region 7a of the bending portion 7 bends from the proximal end side of the first region 7a.

Thus, according to the present embodiment a configuration has been described in which the outer circumferences of the wires 30 that are inserted through the insertion portion 4 are covered by the inside guide pipes 40, the distal ends 40s are fixed to the distal end of the second region 7b of the bending portion 7, and the proximal ends 40k can be switched between a fixed state and a non-fixed state by the fixing switching member 60.

In the configuration described above, the outer circumferences of the inside guide pipes 40 are covered by the outside guide pipes 50, the distal ends 50s are fixed to the distal ends of the flexible tube portion 8, and the proximal ends 50k are fixed at positions that are further to the rear than the proximal end of the flexible tube portion 8.

Thus, by operating the bending operation knob 9 when the proximal ends 40k of the inside guide pipes 40 are not in a fixed state, the entire bending portion 7 bends from the proximal end side of the second region 7b thereof in a manner that takes the distal ends of the outside guide pipes 50 as a starting point. In contrast, by operating the fixing lever 80 and then operating the bending operation knob 9 while the proximal ends 40k of the inside guide pipes 40 are in a fixed state, only the first region 7a of the bending portion 7 bends from the proximal end side of the first region 7a in a manner that takes the distal ends of the inside guide pipes 40 as a starting point. Thus, a bending length can be easily varied using a single bending portion 7 in accordance with the usage situation.

Since only the inside guide pipes 40 and outside guide pipes 50 are provided inside the insertion portion 4, and the bending length of the bending portion 7 can be varied by switching only the proximal ends 40k of the inside guide pipes 40 between a fixed state and a non-fixed state, the configuration that makes the bending length of the bending portion 7 variable is simple.

Further, since the respective inside guide pipes 40 are formed from a flexible member, specifically, a coil pipe, the bending portion 7 can be bent in two stages with a small force.

Thus, with a simple configuration, it is possible to provide an insertion instrument and an endoscope that has a configuration that can vary a bending length using a single bending portion and improve the insertability of an insertion portion.

A modification example of the present embodiment is described hereafter. Although a configuration in which the inside guide pipes 40 and outside guide pipes 50 are constituted by coil pipes is described according to the present embodiment, a configuration may also be adopted in which only either the inside guide pipes 40 or the outside guide pipes 50 are constituted by coil pipes.

In such a case, as described above, a member that does not reduce the bendability of the bending portion 7 and the flexibility of the flexible tube portion 8 and that can resist a compressive force that acts along an extension direction of the guide pipes when the bending portion 7 bends may be selected as a member that constitutes the guide pipes which are not constituted by coil pipes.

Figure 12:
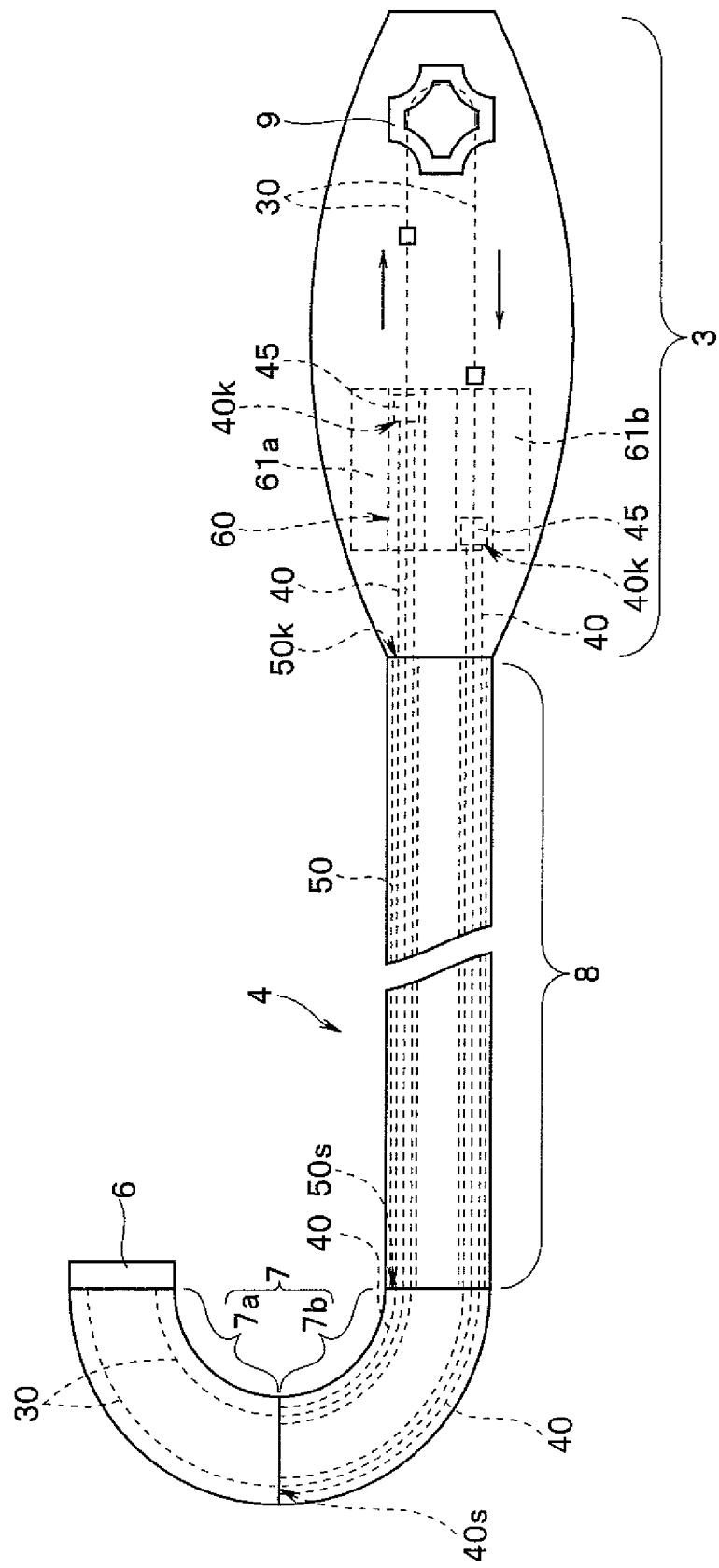
FIG. 12 is a view that schematically shows a state in which, with respect to the bending portion shown in FIG. 2, when a proximal end of an inside guide pipe is in a non-fixed state, a wire is pulled and the entire bending portion is bent from a proximal end side of a second region.
Figure 13:
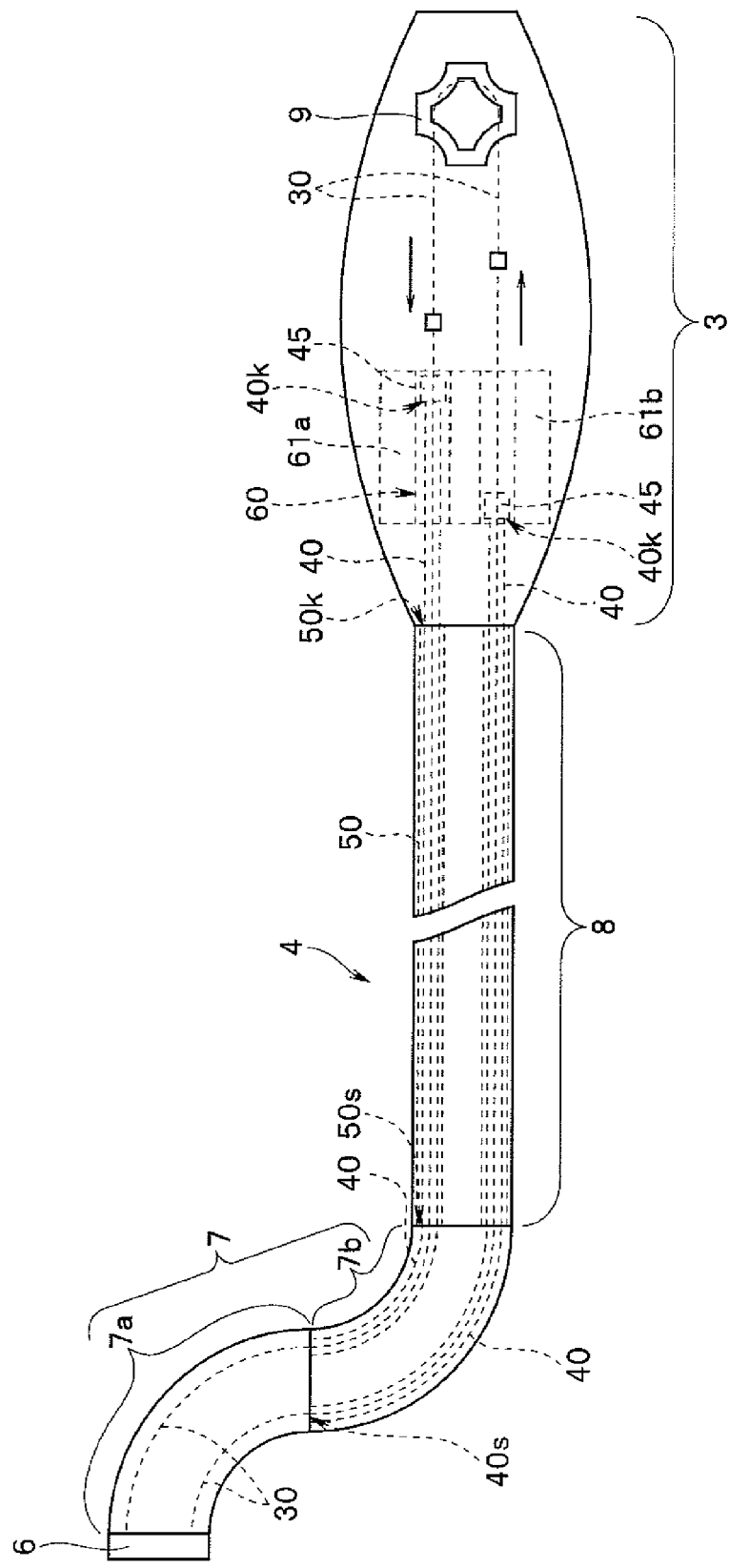
FIG. 13 is a view that schematically shows a state in which the proximal end of the inside guide pipe shown in FIG. 12 is fixed, and a first region of the bending portion shown in FIG. 12 is bent to an opposite side to the bending direction of the second region.

A modification example of the usage method of the present embodiment is described hereunder using FIG. 12 and FIG. 13. FIG. 12 is a view that schematically shows a state in which, with respect to the bending portion shown in FIG. 2, when the proximal ends of the inside guide pipes are in a non-fixed state, a wire is pulled and the entire bending portion is bent from the proximal end side of the second region. FIG. 13 is a view that schematically shows a state in which the proximal ends of the inside guide pipes shown in FIG. 12 are fixed, and the first region of the bending portion shown in FIG. 12 is bent to an opposite side to the bending direction of the second region.

As shown in FIG. 12, when the proximal ends 40k of the inside guide pipes 40 are in a non-fixed state, if any one of the four wires 30, for example, the wire 30 on the upper side, is pulled, the first region 7a and the second region 7b bend upward as described above. More specifically, the entire bending portion 7 bends upwards.

Thereafter, in a state in which the proximal ends 40k of the inside guide pipes 40 are fixed, when the wire 30 on the lower side is pulled, as shown in FIG. 13, because the proximal ends 40k are fixed, in a state in which the second region 7b is fixed in an upward bending shape, only the first region 7a bends downward in the opposite direction to the upward direction from the proximal end side thereof.

Note that the bending directions are not limited to the upward and downward directions. More specifically, in a state in which the second region 7b is bending upward, the first region 7a may be bent to the left or right by pulling the respectively corresponding wire 30. Furthermore, in a state in which the second region 7b is bending to any one of the upward, downward, left, and right sides, the first region 7a may be bent to any one of the upward, downward, left and right sides that is different from the bending direction of the second region 7b.

According to this configuration, since the first region 7a and the second region 7b can be bent in respectively different directions, an effect can be anticipated that facilitates observation and treatment at a place at which it is difficult to view a lesion from the front, such as the gastric cardia, the vicinity of the back of the anus in the rectum, and the back of a fold of the colon. Furthermore, the present configuration allows a surgeon to operate the endoscope simply using only one hand.

Figure 9:
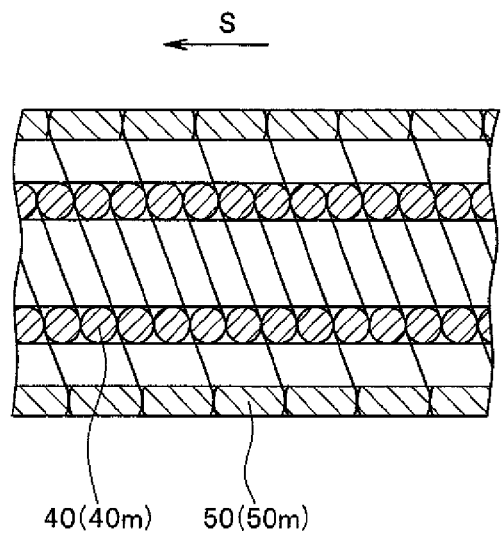
FIG. 9 is a partial cross-sectional view that illustrates a modification example in which an inside guide pipe is constituted by a coil pipe in which an element wire is composed by a round wire coil, and an outside guide pipe is constituted by a coil pipe in which an element wire is composed by a flat wire coil.

Another modification example is described hereunder using FIG. 9. FIG. 9 is a partial cross-sectional view that illustrates a modification example in which an inside guide pipe is constituted by a coil pipe in which an element wire is composed of a round wire coil, and an outside guide pipe is constituted by a coil pipe in which an element wire is composed of a flat wire coil.

As shown in FIG. 9, when the inside guide pipe 40 and the outside guide pipe 50 are constituted by coil pipes, an element wire 40m of the coil pipe constituting the inside guide pipe 40 may be composed of a round wire coil, and an element wire 50m of the coil pipe constituting the outside guide pipe 50 may be composed of a flat wire coil.

Naturally, a configuration may also be adopted in which the element wire 40m of the coil pipe constituting the inside guide pipe 40 is composed of a flat wire coil, and the element wire 50m of the coil pipe constituting the outside guide pipe 50 is composed of a round wire coil.

Furthermore, a configuration may be adopted in which the element wire 40m of the coil pipe constituting the inside guide pipe 40 is composed of a flat wire coil, and the element wire 50m of the coil pipe constituting the outside guide pipe 50 is also composed of a flat wire coil.

Thus, when the inside guide pipe 40 that has been inserted through the inside of the outside guide pipe 50 performs an advancing or retracting movement in the insertion direction S, since it is difficult for the inside guide pipe 40 to become caught on the outside guide pipe 50, the advancing or retracting movement of the inside guide pipe 40 can be performed smoothly.

Figure 10:
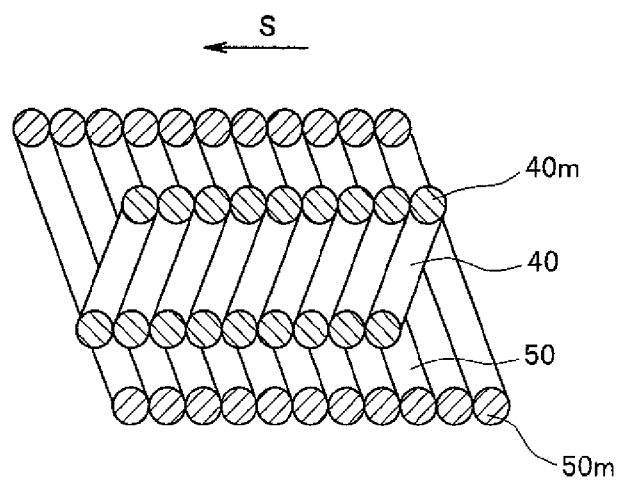
FIG. 10 is a partial cross-sectional view that illustrates a modification example in which a winding direction of a coil pipe constituting an inside guide pipe and a winding direction of a coil pipe constituting an outside guide pipe are mutually opposite directions.

A further modification example is described hereunder using FIG. 10. FIG. 10 is a partial cross-sectional view that illustrates a modification example in which a winding direction of a coil pipe constituting the inside guide pipe and a winding direction of a coil pipe constituting the outside guide pipe are mutually opposite directions.

As shown in FIG. 10, when the inside guide pipes 40 and the outside guide pipes 50 are constituted by a coil pipe, a configuration may be adopted in which the winding directions of the element wires 40m and 50m constituting the respective coil pipes that constitute the inside guide pipes 40 and the outside guide pipes 50 are mutually opposite directions.

Even in this case, when the inside guide pipe 40 that has been inserted through the inside of the outside guide pipe 50 performs an advancing or retracting movement in the insertion direction S, since it is difficult for the inside guide pipe 40 to become caught on the outside guide pipe 50, the advancing or retracting movement of the inside guide pipe 40 can be performed smoothly.

Although examples in which element wires are composed of a coil of round wire or a coil of flat wire are illustrated in FIG. 9 and FIG. 10, naturally the element wire may be any shape as long as the shape is one that makes it difficult for the inside guide pipe 40 to become caught on the outside guide pipe 50.

According to the present embodiment, a configuration has been described in which two kinds of guide pipes, namely, the inside guide pipes 40 and the outside guide pipes 50 are provided inside the insertion portion 4, and the bending portion 7 can be bent in two stages because it is possible to switch a fixed state of the proximal ends 40k of the inside guide pipes 40.

However, the present invention is not limited thereto, and a configuration may also be adopted in which a third guide pipe in which a fixed state of a proximal end thereof that covers the inside guide pipe 40 is switchable is further provided between the inside guide pipe 40 and the outside guide pipe 50.

In this case, by adopting a configuration in which a fixing position of a distal end of the third guide pipe is located further on the proximal end side than the distal end 40s of the inside guide pipe 40, and in which a fixed state of the proximal end of the third guide pipe is switchable in a similar manner to the inside guide pipe 40, it is possible to bend the bending portion 7 in three stages.

In this connection, the number of guide pipes provided between the inside guide pipe 40 and the outside guide pipe 50 is not limited to one guide pipe, and a plurality of guide pipes may be provided therebetween. More specifically, by adopting a configuration in which a fourth guide pipe covers the outer circumference of the third guide pipe, and a fifth guide pipe covers the outer circumference of the fourth guide pipe and so forth, the bending portion 7 can be bent in more than three stages.

In addition, although a configuration is described above in which the bending portion 7 is provided on the distal end side of the insertion portion 4, the present invention is not limited thereto, and the bending portion 7 may be provided at any position in the insertion portion 4.

Figure 11:
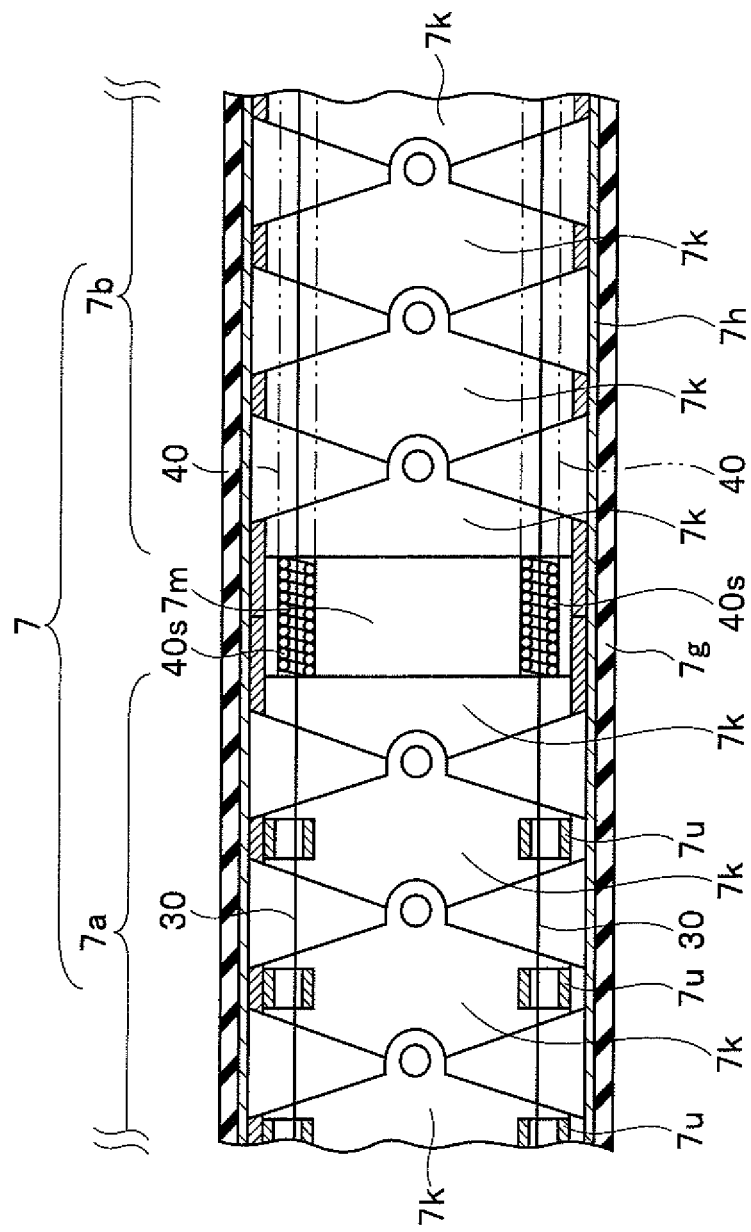
FIG. 11 is a partial cross-sectional view that illustrates a modification example in which a first region and a second region of the bending portion shown in FIG. 2 are connected by a connecting pipe sleeve.

Another modification example is described hereafter using FIG. 11. FIG. 11 is a partial cross-sectional view that illustrates a modification example in which the first region and the second region of the bending portion shown in FIG. 2 are connected by a connecting pipe sleeve.

As shown in FIG. 11, the bending portion 7 may have a configuration in which the first region 7a and the second region 7b are connected along the insertion direction S by a connecting pipe sleeve 7m.

More specifically, the bending portion 7 may have a configuration in which the first region 7a and the second region 7b are connected through a connecting pipe sleeve 7m by fitting a bending piece 7k that is located at a position that is furthest on the proximal end side in the first region 7a and a bending piece 7k that is located at a position that is furthest on the distal end side in the second region 7b into the connecting pipe sleeve 7m that has an outer diameter that is smaller than an inner diameter of the respective bending pieces 7k.

Note that an unshown hole is formed in the bending piece 7k located at the position that is furthest on the proximal end side in the first region 7a and the bending piece 7k located at the position that is furthest on the distal end side in the second region 7b, respectively, and the respective pieces 7K are fastened with an unshown screw or the like that is screwed into an unshown threaded screw hole provided in the connecting pipe sleeve 7m via the aforementioned holes.

In the configuration illustrated in FIG. 11, the distal ends 40s of the four inside guide pipes 40 are fixed by, for example, brazing to the connecting pipe sleeve 7m.

Thus, according to the configuration shown in FIG. 11, in comparison to the present embodiment, because it is sufficient to join the distal ends 40s of the inside guide pipes 40 to the connecting pipe sleeve 7m when joining the distal ends 40s to a midway position of the bending portion 7, the assemblability is improved. Other effects and actions of this modification example are the same as in the present embodiment.

Although an endoscope is adopted as an example of an insertion instrument according to the present embodiment, the present invention is not limited to an endoscope, and can also be applied to other insertion instruments such as a guide tube, various kinds of treatment instruments, and a manipulator as long as the insertion instrument has a bending portion at a distal end of an insertion portion.

What is claimed is:

1. An insertion instrument, comprising:
   an elongated insertion portion that is inserted inside a subject;
   a bending portion that is provided in the insertion portion and that is capable of bending accompanying pulling/relaxing of a wire that is inserted through an inside of the insertion portion;
   a flexible tube portion that is connected in series to a proximal end side of the bending portion in the insertion portion in an insertion direction of the insertion portion;
   an inside guide pipe that is flexible and that is provided inside the insertion portion, and through an inside of which the wire is inserted to freely advance and retract in the insertion direction; and
   an outside guide pipe that is flexible and that is provided inside the insertion portion, and through an inside of which the inside guide pipe is inserted to freely advance and retract in the insertion direction;
   wherein:
   inside the insertion portion, a distal end in the insertion direction of the inside guide pipe is fixed to a midway position in the insertion direction of the bending portion, and a proximal end in the insertion direction of the inside guide pipe is configured such that advancing and retracting in the insertion direction of the inside guide pipe are switchable between a fixed state and a non-fixed state by a fixing switching member; and
   inside the insertion portion, a distal end in the insertion direction of the outside guide pipe is fixed to a distal end of the flexible tube portion, and a proximal end in the insertion direction is fixed at a more rearward position in the insertion direction than the flexible tube portion.

2. The insertion instrument according to claim 1, wherein the bending portion is positioned on a distal end side in the insertion direction in the insertion portion.

3. The insertion instrument according to claim 1, wherein:
   the bending portion comprises a first region on a distal end side in the insertion direction, and a second region that is located further on a proximal end side than the first region; and
   inside the insertion portion, a distal end in the insertion direction of the inside guide pipe is fixed at a distal end position of the second region.

4. The insertion instrument according to claim 1, wherein:
   the bending portion comprises a first region on a distal end side in the insertion direction, a second region that is located further on a proximal end side than the first region, and a connecting pipe sleeve that connects the first region and the second region in the insertion direction; and
   inside the insertion portion, a distal end in the insertion direction of the inside guide pipe is fixed to the connecting pipe sleeve and is fixed at a midway position in the insertion direction of the bending portion.

5. The insertion instrument according to claim 1, wherein, accompanying pulling/relaxing of the wire, in the bending portion:
   when the proximal end of the inside guide pipe is in a non-fixed state, taking the distal end of the outside guide pipe as a starting point, a distal end side of the bending portion that is more forward than the distal end of the outside guide pipe in the insertion direction bends; and
   when the proximal end of the inside guide pipe is in a fixed state, taking the distal end of the inside guide pipe as a starting point, a distal end side of the bending portion that is more forward than the distal end of the inside guide pipe in the insertion direction bends.

6. The insertion instrument according to claim 1, wherein at least one of the inside guide pipe and the outside guide pipe comprises a coil pipe.

7. The insertion instrument according to claim 6, wherein when the inside guide pipe and the outside guide pipe each comprises a coil pipe, a coil pipe comprising the inside guide pipe and a coil pipe comprising the outside guide pipe are configured so that winding directions of element wires comprising the respective coil pipes are mutually opposite directions.

8. The insertion instrument according to claim 6, wherein when the inside guide pipe and the outside guide pipe each comprises a coil pipe, a coil pipe comprising the inside guide pipe and a coil pipe comprising the outside guide pipe are configured so that one of the coil pipes comprises a flat wire coil and another of the coil pipes comprises a round wire coil.

9. The insertion instrument according to claim 6, wherein when the inside guide pipe and the outside guide pipe each comprises a coil pipe, a coil pipe comprising the inside guide pipe and a coil pipe comprising the outside guide pipe both comprise a flat wire coil.

10. An endoscope having a configuration of the insertion instrument according to claim 1.

* * * * *